United States Patent
Jaffe et al.

(10) Patent No.: US 8,176,915 B2
(45) Date of Patent: *May 15, 2012

(54) END-TIDAL GAS ESTIMATION SYSTEM AND METHOD

(75) Inventors: Michael B. Jaffe, Cheshire, CT (US); Joseph A. Orr, Park City, UT (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 791 days.

This patent is subject to a terminal disclaimer.

(21) Appl. No.: 12/270,950

(22) Filed: Nov. 14, 2008

(65) Prior Publication Data

US 2009/0118633 A1    May 7, 2009

Related U.S. Application Data

(63) Continuation-in-part of application No. 12/046,808, filed on Mar. 12, 2008.

(60) Provisional application No. 60/918,189, filed on Mar. 15, 2007.

(51) Int. Cl.
*A61M 11/00* (2006.01)

(52) U.S. Cl. ......... 128/204.23; 128/204.21; 128/204.18; 600/532

(58) Field of Classification Search ............. 600/532, 600/529, 538, 543; 128/204.18, 204.21, 128/204.23
See application file for complete search history.

(56) References Cited

U.S. PATENT DOCUMENTS

| | | | | |
|---|---|---|---|---|
| 5,485,827 | A | * | 1/1996 | Zapol et al. ............. 128/200.14 |
| 5,632,281 | A | | 5/1997 | Rayburn |
| 5,800,361 | A | * | 9/1998 | Rayburn ...................... 600/532 |
| 6,024,089 | A | | 2/2000 | Wallace et al. |
| 6,955,651 | B2 | | 10/2005 | Kuck et al. |
| 2002/0174866 | A1 | | 11/2002 | Orr et al. |
| 2003/0045807 | A1 | | 3/2003 | Daniels, II et al. |
| 2005/0177055 | A1 | | 8/2005 | Kuck et al. |
| 2008/0009762 | A1 | | 1/2008 | Hampton et al. |
| 2008/0091117 | A1 | * | 4/2008 | Choncholas et al. ......... 600/538 |

* cited by examiner

*Primary Examiner* — Steven Douglas

(57) ABSTRACT

An apparatus and method of using an end-tidal gas value taken from an non-intubated patient that includes measuring a plurality of gas concentration values, determining an end-tidal gas value from the gas concentration values, and reporting the end-tidal gas value for a breath as the greater of either: (a) a maximum gas concentration values observed during such a breath, or (b) the end-tidal gas value reported for a previous breath decreased by a maximum allowable breath-to-breath percent change.

12 Claims, 8 Drawing Sheets

END-TIDAL GAS ESTIMATION SYSTEM AND METHOD

CROSS-REFERENCE TO RELATED APPLICATIONS

This application is a Continuation-In-Part (CIP) under 35 U.S.C. §120 of U.S. patent application Ser. No. 12/046,808, filed Mar. 12, 2008, which claims priority under 35 U.S.C. §119(e) from provisional U.S. patent application No. 60/918,189, filed Mar. 15, 2007, the contents of which are incorporated herein by reference.

BACKGROUND OF THE INVENTION

1. Field of the Invention

The present invention pertains to a method and apparatus for providing a reliable end-tidal carbon dioxide ($CO_2$), end-tidal oxygen ($O_2$), or other gas estimation.

2. Description of the Related Art

Respiratory gas monitoring systems typically comprise gas sensing, measurement, processing, communication, and display functions. Such systems are considered to be either diverting (i.e., sidestream) or non-diverting (i.e., mainstream). A diverting gas measurement system transports a portion of the sampled gases from the sampling site, which is typically a breathing circuit or the patient's airway, through a sampling tube, to the gas sensor where the constituents of the gas are measured. A non-diverting gas measurement system does not transport gas away from the breathing circuit or airway, but measures the gas constituents passing through the breathing circuit.

Conventional non-diverting gas measurement systems include gas sensing, measurement and signal processing required to convert the detected or measured signal (e.g., voltage) into a value that may be used by the host system. The gas measurement system communicates with the sample cell placed at the breathing circuit and comprises the components required to output a signal corresponding to a property of the gas to be measured. Placement of the sample cell directly at the breathing circuit results in a "crisp" waveform that reflects in real-time the partial pressure of the measured gas, such as carbon dioxide or oxygen, within the airway. The sample cell, which is also referred to as a cuvette or airway adapter, is located in the respiratory gas stream, obviating the need for gas sampling and scavenging as required in a diverting gas measurement system.

Conventional diverting gas measurement systems utilize a relatively long sampling plastic tube connected to an adapter in the breathing circuit (such as a T-piece at the endotracheal tube or mask connector) or a nasal catheter. The sample gas is continuously aspirated from the breathing circuit or the sample site through the sampling tube and into the sample cell within the monitor at sample flow rates ranging from 50 to 250 ml/min. The location of the sampling port in the breathing varies and may range anywhere from an elbow connected to an endotracheal tube to the wye connector.

Both diverting and non-diverting gas measurement systems include sensors that measure the concentration and/or partial pressure of at least one of the gas components in the sampled gas passing through the sample cell. Two of the most commonly measured gases of clinical importance are carbon dioxide and oxygen. Both diverting and non-diverting gas measurement systems utilize sensors to measure the constituent gases such as carbon dioxide and oxygen.

To measure these gases, electro-optical assemblies are often employed. In the case of a carbon dioxide sensor and a number of other gas sensors, these assemblies includes a source that emits infrared radiation having an absorption band for carbon dioxide. The infrared radiation is usually transmitted along a path that is normal to the flow path of the gas stream being analyzed. Photodetectors are arranged to receive and measure the transmitted radiation that has passed through the gas in the gas stream. Carbon dioxide within the sample gas absorbs this radiation at some wavelengths and passes other wavelengths. The transmitted radiation is converted to signals from which a processor calculates the partial pressure of carbon dioxide. In the case of an oxygen sensor, electrochemical or fluorescence based technologies are often employed.

Carbon dioxide and oxygen are expressed either as a gas fraction ($FCO_2$ and $FO_2$) or partial pressure ($PCO_2$ and $PO_2$). Capnography and oxygraphy, when used without qualification, refers to time-based capnography and oxygraphy. In addition to capnometry, capnography includes a plot of the instantaneous carbon dioxide concentration over the course of a respiratory cycle. From this plot, the cyclic changes can be visualized.

In a "textbook" capnogram 2, an example of which is shown in FIG. 1, the capnogram comprises two segments: an "expiratory" segment 4, and an "inspiratory" segment 6. The expiratory segment consists of a varying upslope 5a that levels to a constant or slight upslope 5b. The inspiratory segment consists of a sharp downslope 7a that settles to a plateau of negligible inspired carbon dioxide 7b. However, other than the end-tidal partial pressure of carbon dioxide, which has been generally understood as the partial pressure of carbon dioxide at the end of expiration, only breathing frequency and a measure of inspiratory carbon dioxide levels are clinically reported. This is the case because only the transition between the expiratory and inspiratory segments can usually be well delineated from a capnogram.

Even then, only if there is substantially no rebreathing, does this transition correspond to the time of the actual beginning of inspiration as delineated by the flow waveform. The transition between inspiration and expiration cannot be readily discerned because of the presence of anatomic dead space that fills with inspiratory gas at the end of expiration. Although the oxygram is not in as widespread clinical use as capnograph, the same issues discussed above apply to the oxygram with the understanding that the oxygram can be considered an inverted version of the capnogram.

If flow is measured in addition to carbon dioxide, the volumetric capnogram can be determined. Similarly if flow is measured in addition to oxygen, the volumetric oxygram can be determined. FIG. 2 illustrates the three phases of a volumetric capnogram. Phase I comprises the carbon dioxide free volume, while phase II comprises the transitional region characterized by a rapidly increasing carbon dioxide concentration resulting from progressive emptying of the alveoli. Phases II and III together are the carbon dioxide containing part of the breath, the effective tidal volume, $V_T$eff. Phase III, the alveolar plateau, typically, has a positive slope indicating a rising $PCO_2$. Using these three phases of the volumetric capnogram, physiologically relevant measures, such as the volumes of each phase, the slopes of phase II and III, and carbon dioxide elimination, as well as deadspace tidal volume and ratios of anatomic and physiologic deadspace can be determined.

One of the objectives when setting the level of mechanical ventilation for a patient is to reach and maintain a desired concentration of arterial carbon dioxide concentration ($PaCO_2$). Because real-time access to $PaCO_2$ measurements is not easy, estimates from a capnogram are used to obtain a surrogate measure. Because of pulmonary shunting, i.e., a portion of the right heart cardiac output reaches the left atrium without having participated in gas exchange, the closest surrogate of $PaCO_2$ that can be obtained from the capnogram is alveolar $CO_2$ concentration ($PACO_2$).

The end-tidal partial pressure of $CO_2$ ($PetCO_2$), usually referred to as the end-tidal carbon dioxide, is used clinically, for example, to assess a patient ventilatory status and, as noted above, has been used by some as a surrogate for $PaCO_2$. Similarly, the end-tidal partial pressure of $O_2$ ($PetO_2$), which may be referred to as the end-tidal oxygen, is also used.

The medical literature is replete with conflicting articles regarding the relationship between $PetCO_2$ and $PaCO_2$, as well as the relationship between changes in $PetCO_2$ and changes in $PaCO_2$. On one hand, Nangia et al. notes that "$ETCO_2$ correlates closely with $PaCO_2$ in most clinical situations in neonates". Similarly, Wu et. al. notes that "we recommend using mainstream capnography to monitor $PetCO_2$ instead of measuring $PaCO_2$ in the NICU." On the other hand, Russell et al. studied ventilated adults and noted "trends in $P(a-et)CO_2$ magnitude are not reliable, and concordant direction changes in $PetCO_2$ and $PaCO_2$ are not assured."

Researchers have considered maneuvers to improve 'prediction' of $PaCO_2$. Tavernier et al. studied whether prolonged expiratory maneuvers in patients undergoing thoracoabdominal oesophagectomy improved the prediction of $PaCO_2$ from $PetCO_2$ and concluded that these maneuvers did not improve estimation. A commonly held belief among critical care physicians is that end-tidal $CO_2$ cannot be used as a surrogate for either arterial $PCO_2$ or changes in arterial $PCO_2$. To complicate matters further Chan et al. noted that "mainstream $PetCO_2$ provided a more accurate estimation of $PaCO_2$ than side-stream measurement."

If end-tidal $PCO_2$ could be reliably used as a surrogate for arterial $CO_2$, arterial blood sampling could be reduced, applications that currently use intermittent blood sampling would become more clinically acceptable, and applications, such as closed loop control of ventilation (particularly non-invasive ventilation), would be more viable. Therefore, techniques for reliability and/or indicating the reliability of end-tidal $PCO_2$ estimations are desired.

SUMMARY OF THE INVENTION

Accordingly, it is an object of the present invention to provide a method of using an end-tidal gas value that as a surrogate for arterial gas value when measuring the end-tidal gas value in a non-intubated patient that overcomes the shortcomings of conventional end-tidal gas value measurement techniques. This object is achieved according to one embodiment of the present invention by providing a method that includes (1) measuring a plurality of gas concentration values, (2) determining an end-tidal gas value from the gas concentration values, and (3) reporting the end-tidal gas value for a breath as the greater of either (a) a maximum gas concentration values observed during such a breath, or (b) the end-tidal gas value reported for a previous breath decreased by a maximum allowable breath-to-breath percent change.

It is a further object of the present invention to provide an apparatus that indicates the reliability of an end-tidal gas value that overcomes the shortcomings of conventional end-tidal $CO_2$ measurement techniques when used on a non-intubated patient. This object is achieved according to one embodiment of the present invention by providing an apparatus comprising a means for sensing a plurality of gas concentration values; a means for determining an end-tidal value from the gas concentration values; and a means for reporting the end-tidal gas value for a breath as the greater of either: (a) a maximum gas concentration values observed during such a breath, or (b) the end-tidal gas value reported for a previous breath decreased by a maximum allowable breath-to-breath percent change.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

The present invention addresses the known problems with the studies to date including (a) the lack of a clear definition of end-tidal gas value, (b) how end-tidal gas values relate to arterial gas values in both 'stable' and 'unstable' ventilatory patterns, and, (c) an understanding of when end-tidal gas values will and won't be a reliable correlate of arterial and or alveolar gas values. The present invention addresses the need to provide more reliable end-tidal gas values. It should be noted that the while most of the present discussion takes place with reference to carbon dioxide ($CO_2$), the methods described herein apply to other gases as well, including but not limited to respiratory gases, such as oxygen, nitrous oxide, nitric oxide, and other gases, such as anesthetic agents. To determine a more reliable end-tidal gas value, it is important to delineate properly the end-tidal gas value and to determine the reliability of that estimate.

Figure 3:
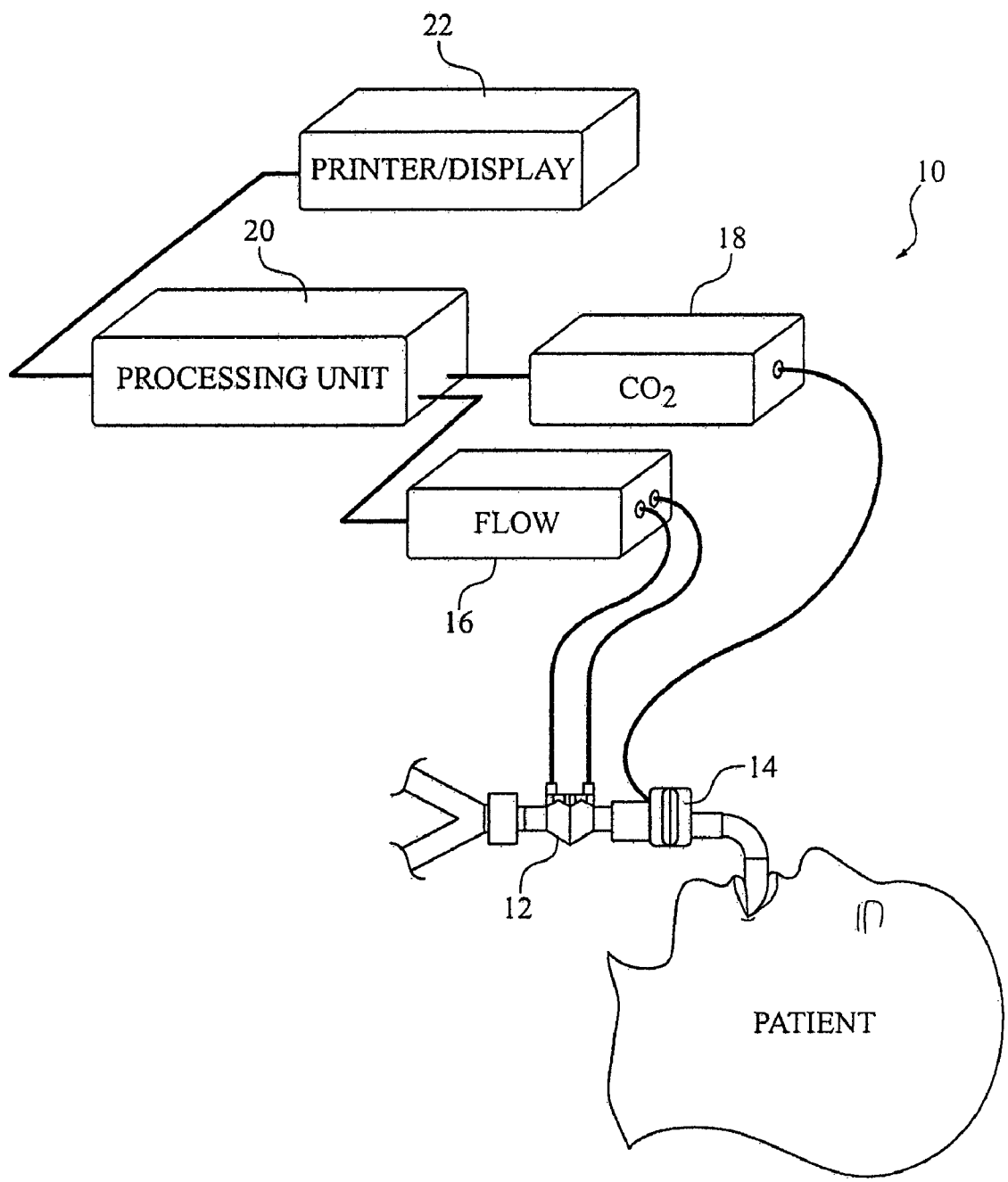
FIG. 3 is a schematic illustration of a gas measurement system in accordance with an exemplary embodiment of the present invention.

An exemplary embodiment of a gas measurement system 10 suitable for use in the present invention is illustrated in FIG. 3. The illustrated exemplary embodiment of system 10 comprises a differential pressure flowmeter 12, a flow signal unit 16, a gas sensor 14, a $CO_2$ signal unit 18, a processor or processing unit 20, and a data display 22. System 10 can be used alone or in combination with mechanical ventilation of the patient. It can be a stand-alone monitoring system or integrated with a ventilator.

The exemplary device for respiratory flow measurement is differential pressure flowmeter 12, which provides a pressure differential indicative of respiratory flow; the differential pressure being converted via pressure transducers in flow signal unit 16 to electrical signals representative of the relationship between respiratory flow and pressure differential. An exemplary differential pressure flowmeter is manufactured and sold by Respironics, Inc., Wallingford, Conn. However, any flow measurement devices may be utilized, including flow sensors based on other flow measurement techniques, such as optical, vanes, sonic, etc.

Sensors capable of measuring carbon dioxide content in a gas sample are well known. An exemplary device for measuring carbon dioxide content is a gas analyzer of the type employing non-dispersive infrared radiation, which presents data representing the % $CO_2$ (or $pCO_2$) of a sample of exhaled breath. Other technologies used to measure the concentration of carbon dioxide, such as electrochemical technologies, Raman spectroscopy, and mass spectroscopy, can also be used in the present invention. The exemplary gas sensor 14 capable of measuring carbon dioxide content in a patient's exhaled breath is available from Respironics, Inc., Wallingford, Conn., under the trade name CAPNOSTAT®. It is to be understood, however, that other methods of measuring carbon dioxide content, either at the airway (non-diverting) or by removing a sample (diverting), may be used in the present invention.

Figure 4:
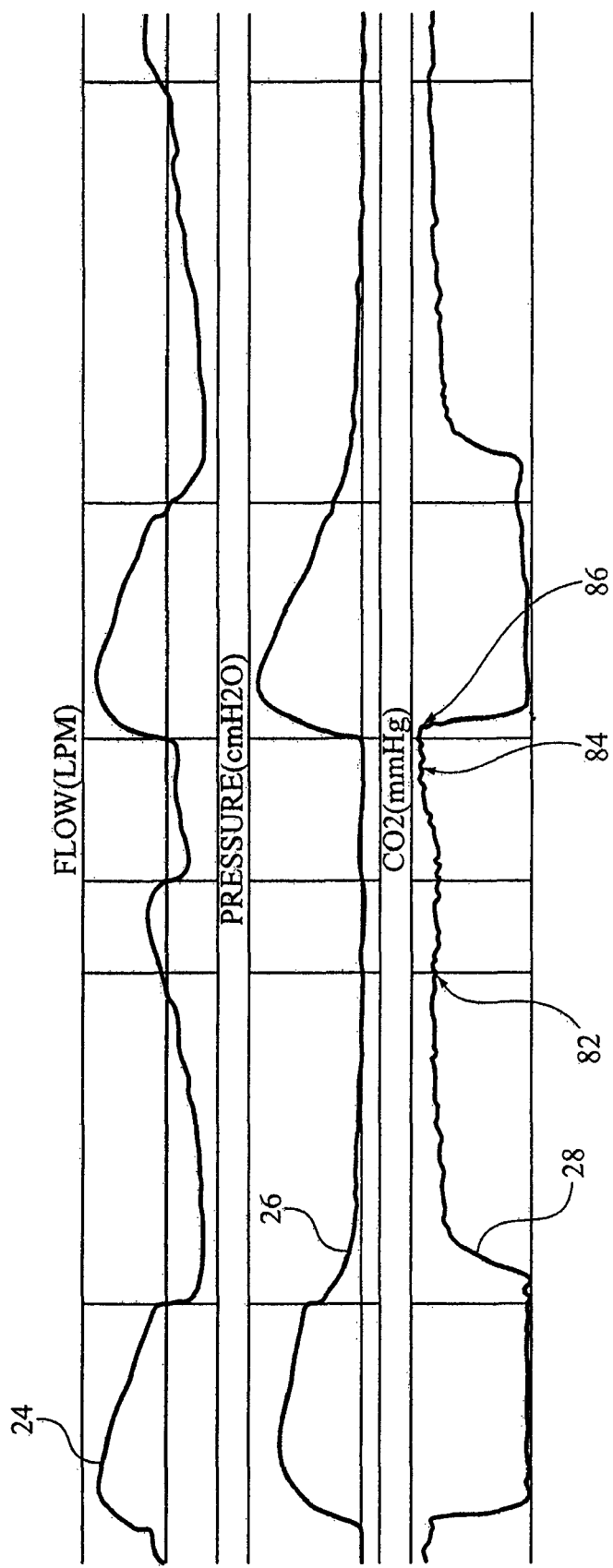
FIG. 4 is a chart illustrating flow, pressure, and $CO_2$ measurements of a patient.

FIG. 4 illustrates one of the problems determining a repeatable and reliable end-tidal value with a plot of flow 24, pressure, 26 and $CO_2$ 28 as a function of time for two "breaths" with ventilator-patient asynchrony. The measured value of the $PetCO_2$ depends upon how $PetCO_2$ value is defined. For example, depending on how end-tidal $CO_2$ is determined, it could be reported as either 27, 30 or 31 mm Hg. In FIG. 4, $PetCO_2$ at position 82 is 27 mm Hg, at position 84 is 31 mm Hg, and at position 86 is 30 mm Hg. The end of expiration, as defined by the flow waveform (position 82), results in an end-tidal value of 27 mm Hg. However, using the apparent expiration-inspiratory transition-position 86 from the capnogram alone results in $PetCO_2$ of 30 mmHg. On the other hand, if the largest value is used (position 84) a $PetCO_2$ of 31 mm Hg is obtained.

Conventionally, the concentration towards the end of phase III of the time or volumetric capnogram is considered the good estimator of alveolar $CO_2$ concentration (i.e. $PetCO_2$) and is usually determined on a breath-by-breath basis. As noted earlier, the simplest approach to determining $PetCO_2$ is simply to use the maximum value which would generally occur during phase III. Because extreme values are often sensitive to artifact or noise, other approaches may use an average over the last part of phase III, where the 'last part' can be defined either in terms of time or in terms of expiratory volume.

The present invention, unlike these other techniques, contemplates using the flow and/or pressure waveform to better delineate the end of expiration, especially, if significant rebreathing is present, so that the end-tidal gas value may be simply and repeatably determined. Similarly, because volume is the integral of flow, the volumetric capnogram may also be used as well to better delineate the end of expiration (see below). If the flow waveform or a surrogate is not available, the present invention contemplates using a waveform shape analysis to better delineate the end of expiration.

Figure 5:
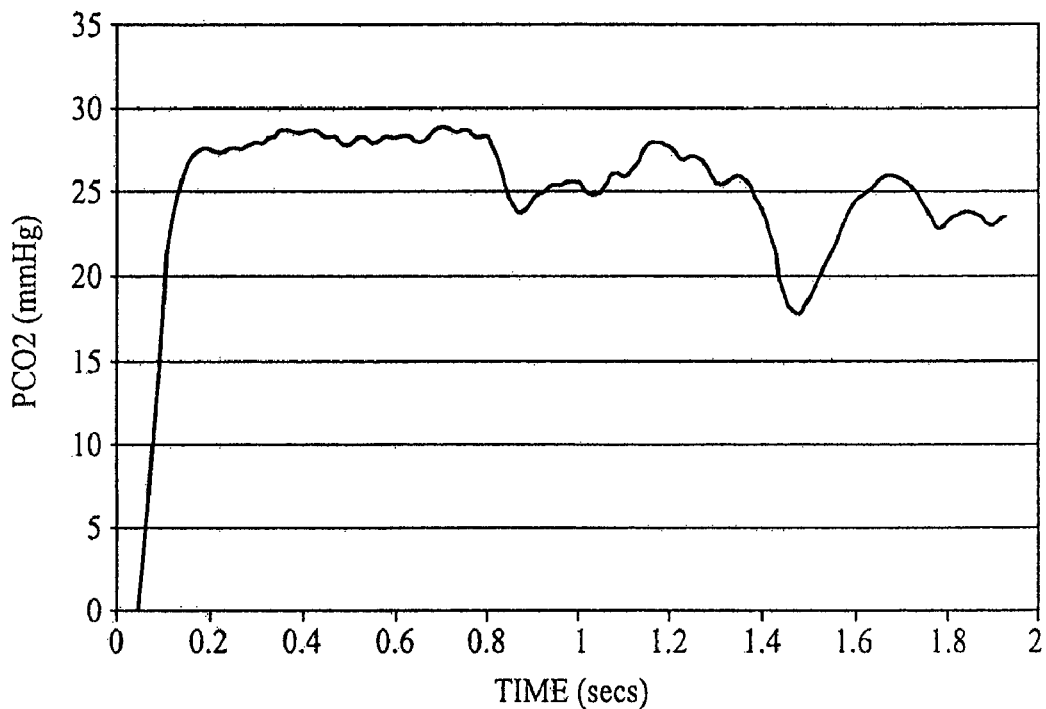
FIG. 5 is an exemplary time-based capnogram with a long expiratory pause.
Figure 6:
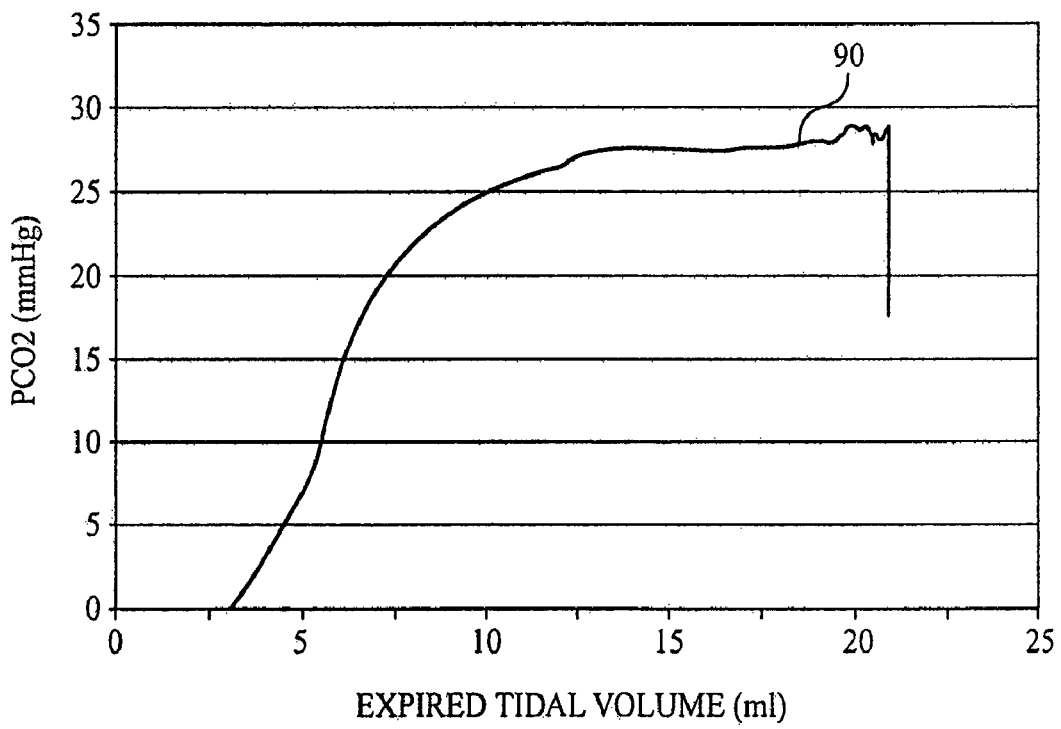
FIG. 6 is exemplary volumetric capnogram of the waveform in FIG. 5.

FIGS. 5 and 6 are time-based and volumetric capnograms illustrating the potential difficulty of obtaining an end-tidal value from a time based capnogram alone. FIG. 5 illustrates a phenomenon often seen in neonates with long expiratory pauses due to the I:E ratios of 1:8-1:10 during which very minor inspiratory efforts are made resulting in a capnogram that is difficult to interpret. Examining such a time-based capnogram makes it very difficult to determine an end-tidal value. However, comparing the time-based and volumetric-based capnograms in FIGS. 5 and 6 allows for some clarity. Note that the ventilation-perfusion relationships of the lung are more accurately reflected in the slope of phase III by a volumetric capnogram than in that of a time-based capnogram in which the gradient of the phase III slope is usually less obvious and can be misleading. This may be because a smaller volume of expired gases (approximately the final 15%) often occupies half the time available for expiration, so that a similar change in the $CO_2$ concentration is distributed over a greater length of time in the time-based capnogram than in the volumetric capnogram.

In FIG. 6, the plot of the expired volume vs. the partial pressure of $CO_2$ during expiration clearly shows a plateau 90 from which an end-tidal value may be determined using a variety of methods. All of the parameters associated with volumetric capnography can also be determined. For example, the end-tidal gas value may be determined by computing the average $PCO_2$ value for the last X % of volume (such as 5 or 10%), fitting the curve, or a portion of it, to a model (physiologically based such as one based on Weibel model or empirical). Using a model based approach to fit the concentration-volume curve allows for potentially clinically relevant values to be determined.

In addition to the challenges already outline, one of the primary challenges in the determination and clinical use of $PetCO_2$ values comes from an implied assumption, that $PetCO_2$ represents the average value of the alveolar $CO_2$ concentration ($P_ACO_2$). As $CO_2$ continues to pass from the blood into the alveolar gas phase during expiration, the alveolar $CO_2$ concentration rises during expiration. During inspiration, $CO_2$ free gas serves to dilute the alveolar gas and the alveolar $CO_2$ concentration decreases. The shape of the respiratory flow waveform (e.g., tidal volume, inspiratory to expiratory time ratio), the pulmonary capillary blood flow, the venous $CO_2$ concentration, the amount of deadspace, and the serial and alveolar deadspace affect the particular shape of the alveolar $CO_2$ concentration waveform. This shape, in turn, affects the average alveolar $CO_2$ concentration. The very last part of the expired volume that leaves the lungs, never reaches gas sensor 14, but remains in the anatomical and apparatus (serial) deadspace.

Figure 8B:
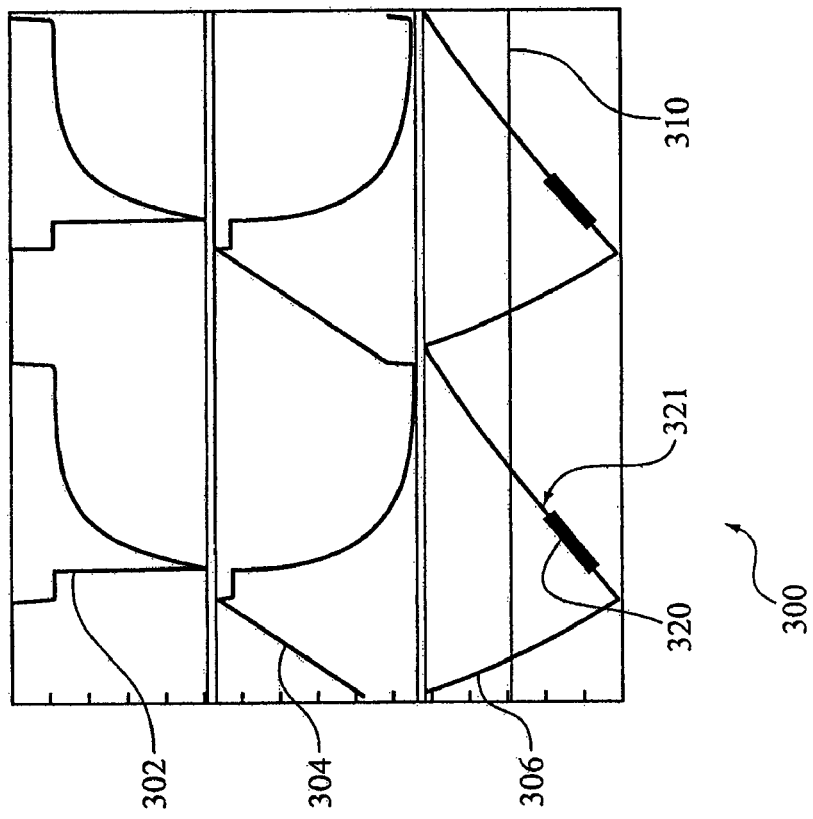
FIGS. 8A and 8B are plots of simulated flow, volume, and alveolar $CO_2$ concentrations.
Figure 8A:
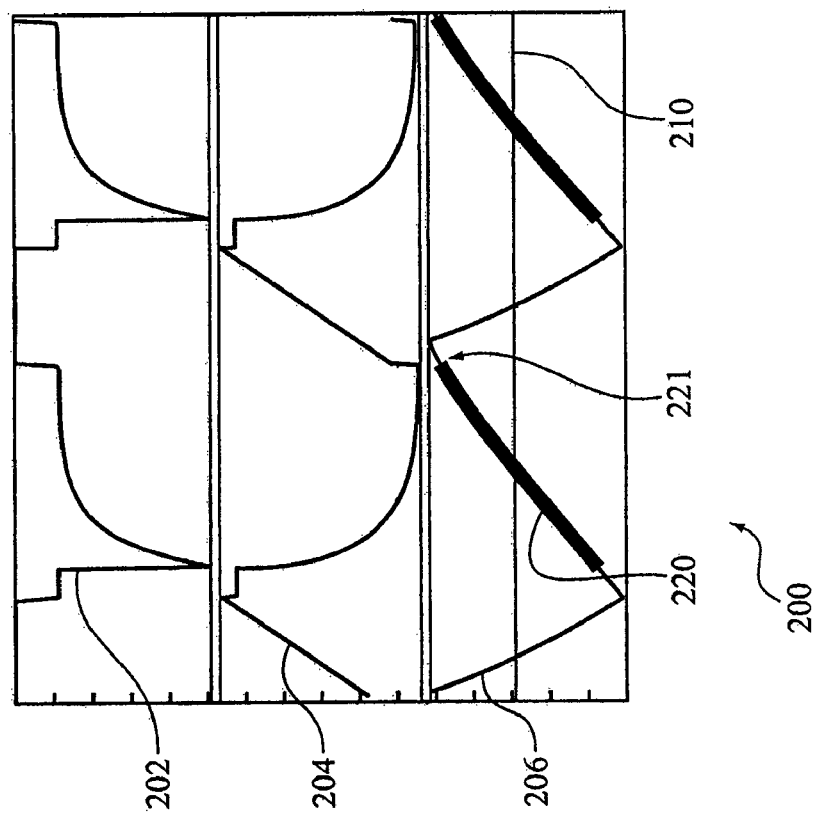

The simulation shown in FIGS. 8A and 8B, which show simulated flow 202, volume 204, and alveolar $CO_2$ concentration 206 waveforms illustrate how this can affect the $PetCO_2$ and its relationship to average alveolar $CO_2$ concentration. Lines 210 and 310 in alveolar $CO_2$ concentration graphs 206 and 306 indicate the average alveolar concentration. Thickened lines 220 and 320 of alveolar $CO_2$ concentration graphs 206 and 306 illustrate portions of the alveolar waveform that is measured by gas sensor 14 in the form of a capnogram. End portions 221 and 321 of the thickened lines 220 and 320 are conventionally reported as $PetCO_2$.

FIG. 8A illustrates the waveforms that would be observed if there was no serial deadspace between the alveoli and gas sensor 14. The resulting $PetCO_2$ value (end portion 221) would overestimate average alveolar $CO_2$ in this simulation.

FIG. 8B illustrates the waveforms which would be observed if there was a normal serial deadspace (e.g., 150 ml) between the alveoli and gas sensor 14. The resulting PetCO$_2$ value (end portion 321) would underestimate average alveolar CO$_2$ in this simulation. The step size of the alveolar CO$_2$ concentration graphs 206 and 306 are approximately 4 mmHg. Larger deadspaces and smaller tidal volumes can increase the difference between PetCO$_2$ and average alveolar CO$_2$ concentration. Also, this effect may increase noise in PetCO$_2$ signal due to breath-to-breath variations in tidal volumes of spontaneously breathing patients.

Figure 9B:
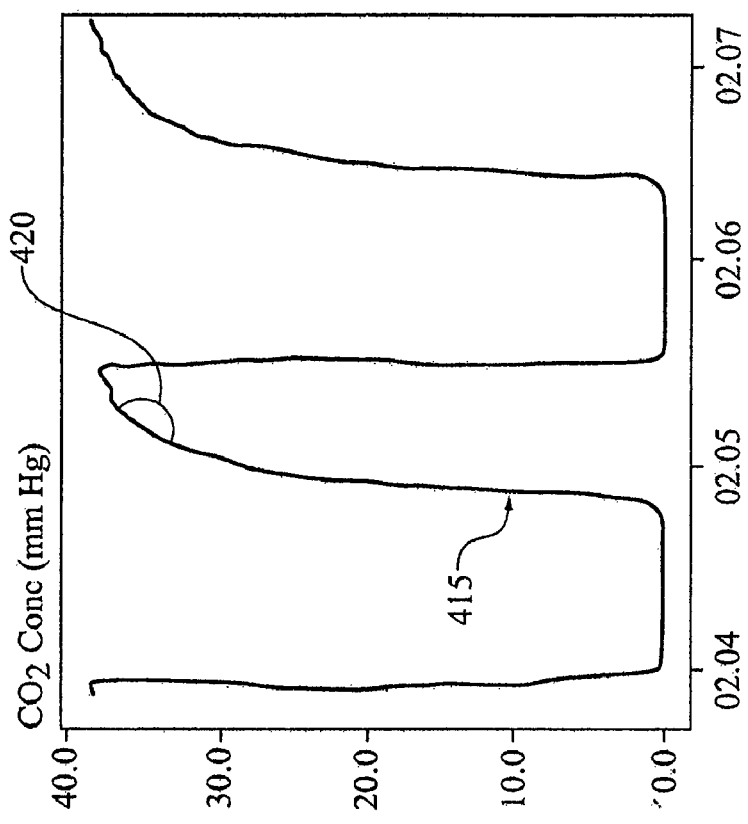
FIG. 9B is a time-based capnogram recorded with a face mask.
Figure 9A:
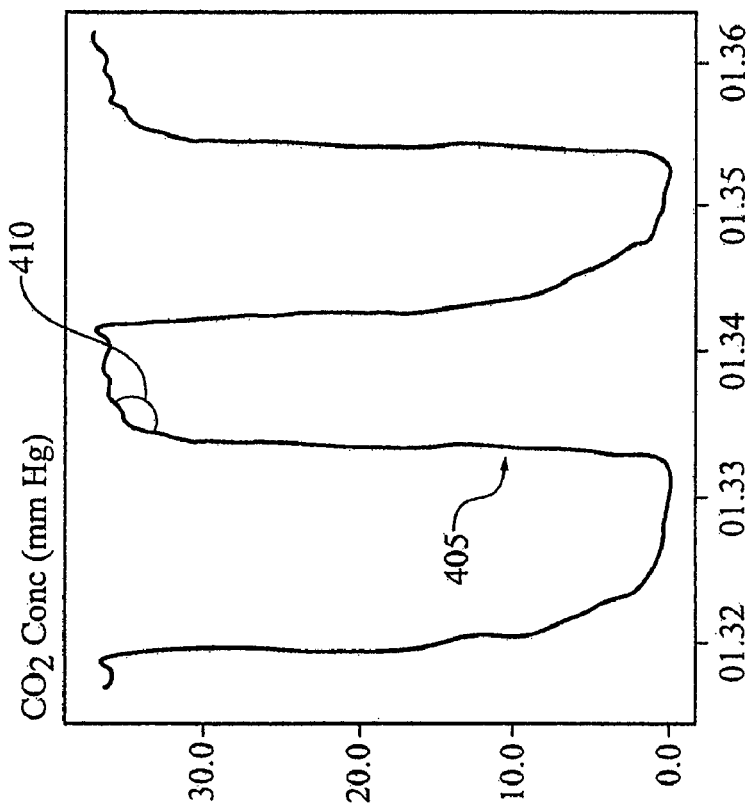
FIG. 9A is a time based capnogram recorded with a mouthpiece.

In patients who breathe through a face mask (instead of an endotracheal tube), the capnogram is additionally affected by the "smearing" effect of the face mask volume—again exacerbated by small or varying tidal volumes. This "smearing" effect is shown in FIGS. 9A and 9B. In FIG. 9A, the patient is breathing with through a mouthpiece resulting in alpha angle 410 of capnogram 405, which is only slightly larger than 90 degrees. In addition, capnogram 405 has as a relatively flat phase III. In FIG. 9B, the same patient is breathing through a face mask resulting in alpha angle 420 of capnogram 415 that is more obtuse than angle 410. In addition, phase III of capnogram 415 is more rounded than in capnogram 405, primarily due to the dilution and mixing in the deadspace volume of the face mask. Generally, the differences between PetCO$_2$ and average alveolar CO$_2$ concentration are relatively small in most subjects (e.g., on the order of 2 or 3 mmHg) without serious ventilation-perfusion abnormalities. If, however, PetCO$_2$ is used to extract additional information, such as with partial CO$_2$ rebreathing maneuvers, these small differences may become significant.

The present invention contemplates approximating expiratory volumetric capnograms using mathematical functions. This is especially helpful when attempting to obtain a capnogram under adverse conditions, such as those noted above, as well as in the presence of large noise (physiological and instrumental). An exemplary mathematical function that may be used to approximate an expiratory volumetric capnogram is a power function of the following form:

$$invCO_2 = f \times V_E^n,$$

where: $invCO_2 = CO_2 - maxCO_2$, CO$_2$ is the expired CO$_2$ as measured by the gas sensor, $V_E$ is the expired volume, f and n are approximation parameters, and maxCO$_2$ is constant CO$_2$ value, which is another approximation parameter.

The approximation parameters f and n can be found by known numerical methods, including linear regression of natural log ($invCO_2$) vs. natural log (VE). The approximation parameter maxCO$_2$ can be found iteratively using known search algorithms or using more generalized least-squares algorithms than conventional linear regression.

Figure 10:
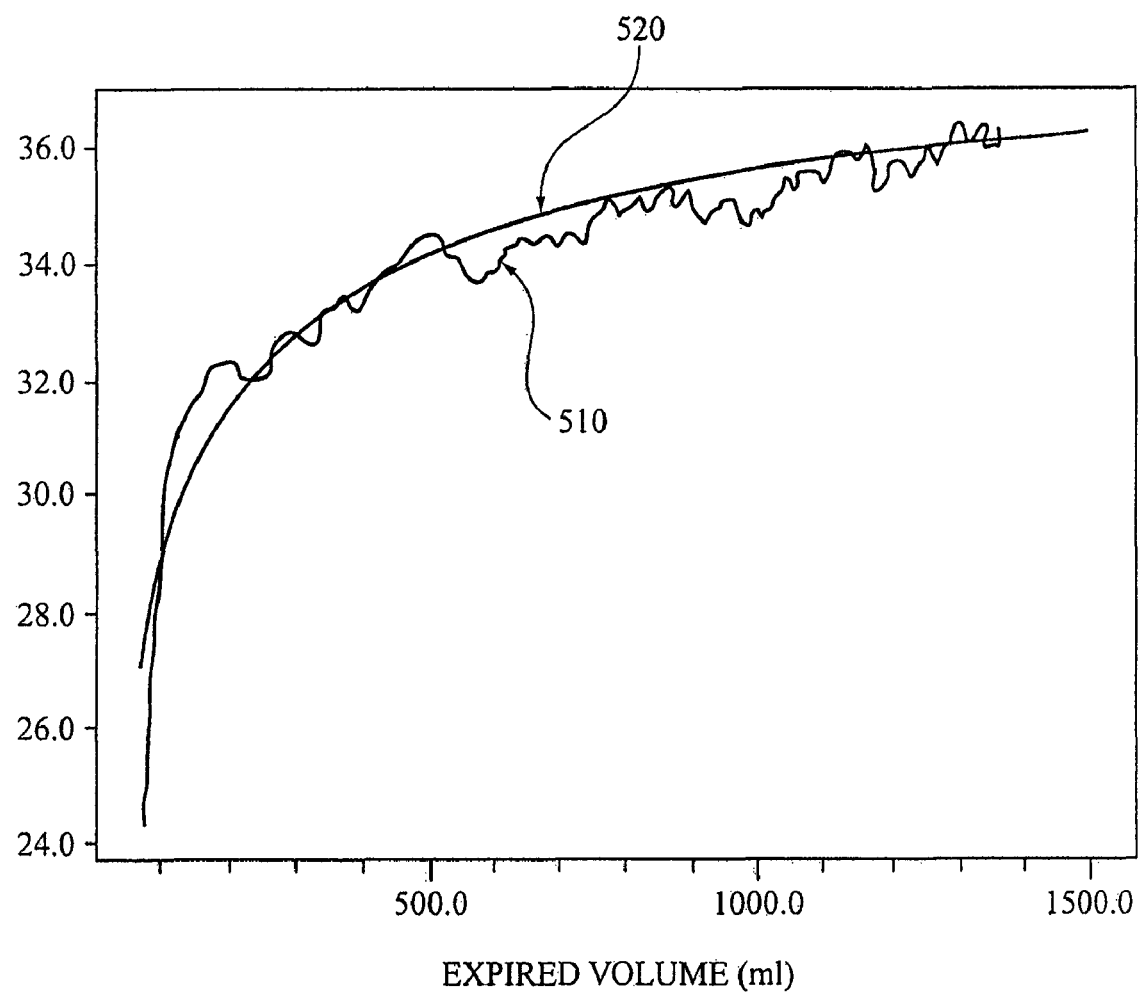
FIG. 10 is a volumetric capnogram and an associated power regression approximation curve.

FIG. 10 shows an example of an original capnogram 510 approximated by a power regression curve 520. A number of approaches are contemplated to determine an PetCO$_2$-equivalent value from this power regression approximation. In general, the PetCO$_2$ value should be more representative of the alveolar CO$_2$ concentration, if the tidal volume is large. If the tidal volume is small, the power regression approximation may be used to extrapolate to what the capnogram value would have been at a larger expiratory volume. Alternatively, the power regression approximation may be used to report the PetCO$_2$ concentration at one constant expired volume for all breaths, regardless whether they are small or large.

The present invention contemplates that the model derived PetCO$_2$ values could be used replace conventionally determined PetCO$_2$ values in conventional CO$_2$ monitors, as well as replace conventionally determined PetCO$_2$ values for differential CO$_2$ Fick determination of pulmonary capillary blood flow. Other approximation functions, other than the power function described above, are contemplated as well. The approximation parameters may be found by methods known in the art including, but not limited to, linear regression, least square algorithms, artificial neural networks and iterative search algorithms. The algorithm to find the approximation parameters may also consider approximation results from previous breaths to make finding the approximation parameters for the current breath faster, less computationally expensive, and more accurate.

Figure 7:
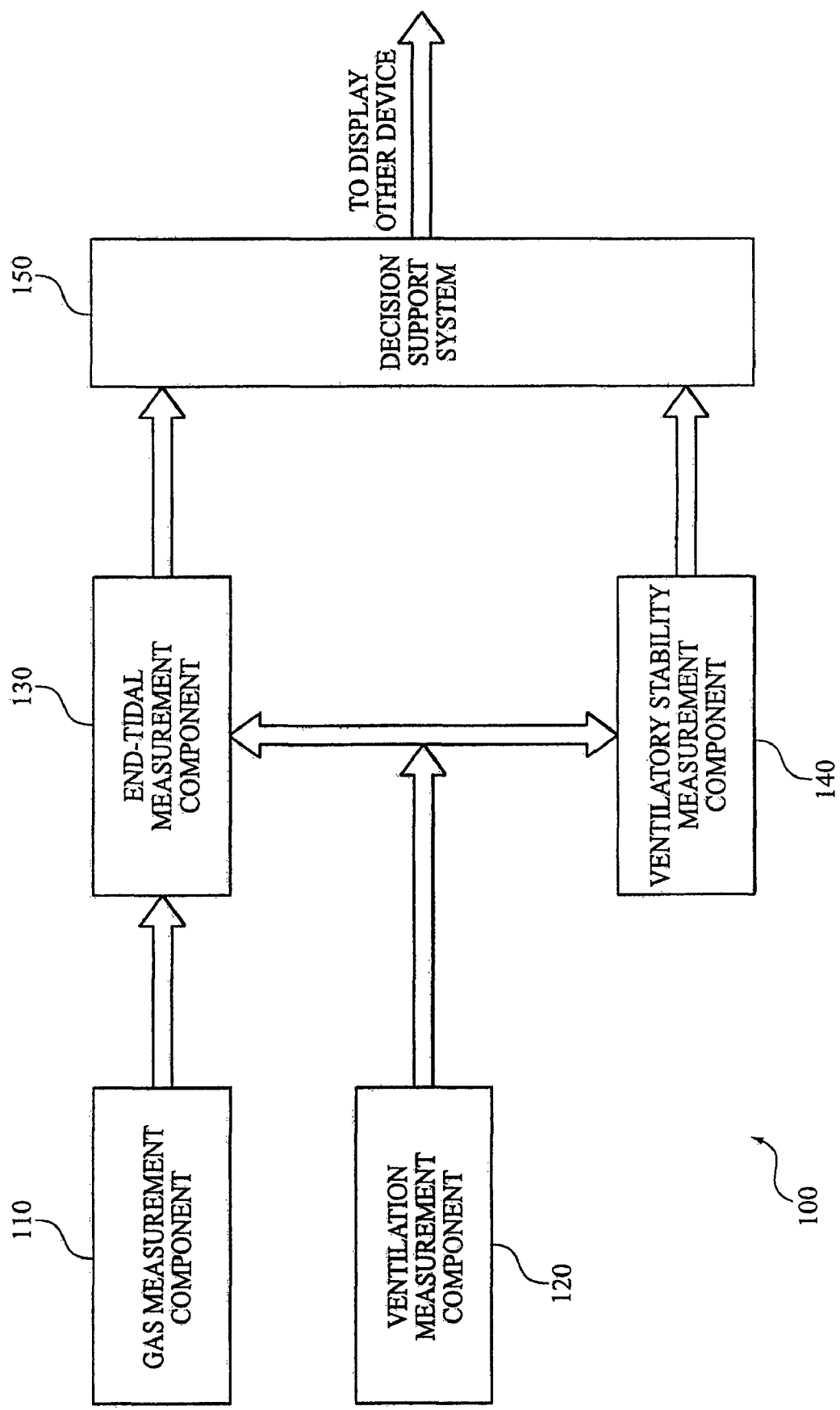
FIG. 7 is a schematic diagram of an exemplary apparatus suitable for implementing the process of the present invention.

The present invention contemplates providing a better definition of when end-tidal CO$_2$, however it may be determined, is a reliable/viable estimate of arterial CO$_2$ and when it is not a reliable/viable estimate of arterial CO$_2$. This may be related to both the physiological status of the patient's cardio-pulmonary system and the recent pattern of ventilation, which may have significantly affected the lung and blood stores of the patient. Therefore, estimation of $V_d/V_t$ physiologic/alveolar or a surrogate to assess the degree of impairment and the assessment of the degree of disturbance to the CO$_2$ stores would permit the end-tidal CO$_2$ value to be determined and displayed with greater confidence. FIG. 7, which is discussed in greater detail below, illustrates an exemplary process and apparatus for providing an indication of when end-tidal CO$_2$ is or is not a reliable/viable estimate of arterial CO$_2$.

The present invention also contemplates determining the degree of physiological impairment. Vd/Vt physiologic is preferably estimated using alveolar partial pressure of CO$_2$ ($P_ACO_2$) (per its definition without the Enghoff modification). $P_ACO_2$ may be estimated by application of models to the volumetric capnogram as well as neural networks, genetic algorithms, and other approaches or combination of approaches. U.S. Pat. No. 5,632,281 describes an approach for arterial estimation that may be used for alveolar estimation. VDalv/Talv may be used as well and Hardman et al. describes a method for estimating this ratio.

Figure 1:
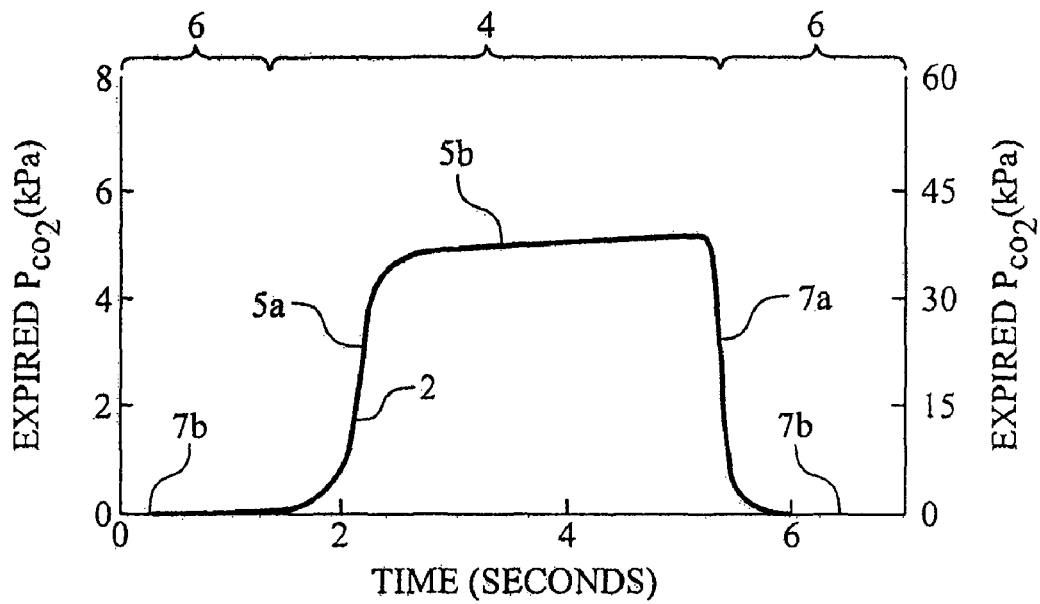
FIG. 1 is a graph of an exemplary time-based capnogram.
Figure 2:
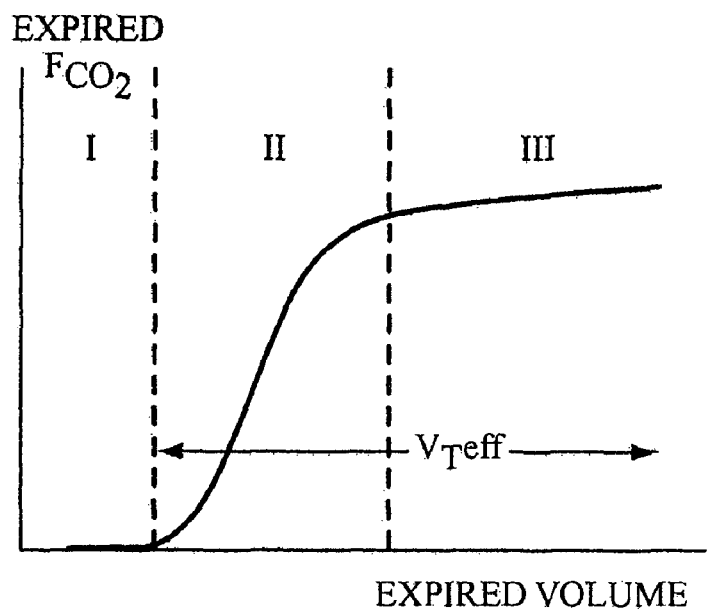
FIG. 2 is a graph of an exemplary volumetric capnogram.

The present invention also contemplates determining the degree of disturbance. The degree of disturbance or ventilatory stability can be assessed by different methods. For example, assessment of the degree of disturbance to the CO$_2$ stores may be determined by the measurement of ventilation (with the use of a model) to better determine periods of 'stability.' Methods of estimating CO$_2$ stores may be found in U.S. Pat. No. 6,955,651 ("the '651 patent"), the contents of which are incorporated herein by reference. The tidal volume must be sufficient size relative to the anatomic deadspace. Functional anatomic deadspace may be estimated by methods known in the art such as Fowler's method. The reliability of the end-tidal value is further increased by applying criteria based on the expiratory flow rate for the breath from which the end-tidal measurement is taken. Application of these criteria will help allow the determination of a reliable end-tidal value As noted above, FIG. 7 illustrates an exemplary schematic embodiment of a gas measurement system 100 according to the principles of the present invention. Gas measurement system 100 illustrates the components of a system used to provide a reliable estimate of the end-tidal concentration of a gas. The gas concentration or partial pressure values (used interchangeably) are determined by gas measurement component 110. This may be determined on a continuous or intermittent basis. Conventional gas concentration component provide data sampled at sampling rates from 25 to 100 samples/sec. Gas measurement component 110 corresponds, for example, to gas sensor 14 and CO$_2$ signal unit 18 in FIG. 1 as discussed above.

Ventilation values measured at the airway or via other technologies are determined by ventilation measurement component 120. Ventilation values includes, but are not limited to flow, volume, pressure, temperature, and humidity or any combination thereof. The ventilation values may be determined on a continuous or intermittent basis. Ventilation measurement component 120 corresponds, for example, to differential pressure flowmeter 12 and flow signal unit 16. In an exemplary embodiment, the ventilation related values are determined by measurements of flow, volume, or surrogates thereof. Surrogates of flow derived from acoustic measurements from external surface sensors from companies, such as Andromed, are contemplated.

The gas concentration values from gas measurement component 110 and ventilation measurement component 120 are received by the end-tidal gas measurement component 130. The present invention contemplates implementing end-tidal gas measurement component 130 via processing unit 20 of FIG. 1. Characteristics of the received ventilation values are used by the end-tidal gas measurement component 130 to derive a more robust end-tidal gas value from the gas concentration values. For example, changes in the received ventilation values indicating the change from expiratory flow in the airway to inspiratory flow would be used to delineate in time the end of expiration. This may be obtained from the values of the flow, volume or surrogates thereof. For flow, the time of the zero crossing from expiratory flow (or zero flow in the case of a pause interval) to inspiratory flow may be used. For volume, the time from volume increasing (or flat) to decreasing may be used. Similarly, for acoustic measurements the change from expiratory to inspiratory flow can be determined by known methods.

Values from the ventilation measurement component 120 are also received by the ventilatory stability measurement component 140. The present invention also contemplates implementing ventilatory stability measurement component 140 via processing unit 20 of FIG. 1. Ventilatory stability may be determined by evaluating an historical record of ventilation values and assessing its stability. Time periods for assessment would vary based by the size of the gas stores of the gas in question. For $CO_2$ and $O_2$, the gas stores that would be considered are both the lung and blood stores. The time interval that would be assessed would be based upon size of those stores which could be estimated via methods as disclosed the '651 patent as well as rules of thumb based upon patient size. Exemplary methods of determining the variability of the ventilation values over the time period for assessment include analysis of the distribution of tidal volume values and, if a period of significant hyperventilation or hypoventilation is observed during the assessment period, then the end-tidal value would be deemed less reliable. The present invention also contemplates that the ventilatory stability measurement component 140 would receive values from the gas measurement component 110.

The estimates of ventilatory stability from the ventilatory stability measurement component 140 and the end-tidal values from end-tidal measurement component 130 are received by decision support system 150. The present invention further contemplates implementing decision support system 150 via processing unit 20 of FIG. 1. Using these values as well as other criteria, decision support system 150 determines the reliability of the end-tidal value. The reliability may be based simply on a threshold of ventilatory stability and may be indicated on the display of the host system numerically or graphically. The end-tidal number may be color coded to indicate its reliability such as red, yellow, green for unreliable, questionable, reliable, respectively. Based upon input from user or another system, decision support system 150 may be configured as a rule based system. For example, patient age as well as disease could permit physiological bounds (either fuzzy or hard bounds) to be used to indicate the reliability of the end-tidal value. It is also contemplated using measurement of Vd/Vt as noted earlier, in decision support system 150 to determine reliability of the end-tidal value. This could be simply an additional rule such as, in the case of Vd/Vt physiologic, if Vd/Vt physiologic >0.70 then the end-tidal $CO_2$ value is highly unreliable as surrogate of arterial $CO_2$.

The present inventors recognized that for a non-intubated patient, acquisition of a non-diluted sample of pure alveolar gas is more difficult and for an intubated patient. Table 1 below lists some of the sources of error that can arise when using a sampling capnometer to monitor respiration in the non-intubated patient during procedural sedation, patient controlled anesthesia, or in other conditions in which insufficient respiration is likely.

TABLE 1

| Source of etCO2 error | Effect on measured PetCO$_2$ | Effect on Alveolar CO$_2$ (PACO$_2$) and arterial CO$_2$ (PaCO$_2$) |
|---|---|---|
| Inadequate breath size (breaths must be large enough to clear anatomic dead space) caused by respiratory arrest, obstructive disorder, etc. | PetCO$_2$ will read low relative to PACO$_2$. The amount of this error will possibly change drastically from breath to breath. | PACO$_2$, PaCO$_2$ increases until new steady state is reached. |
| Cardiogenic oscillations during long end-expiratory pause (associated with respiratory arrest) | Oscillations are confused with breaths. PetCO$_2$ measured from these oscillations may be equal to the true PetCO$_2$ during first 1-2 oscillations and then read lower as oscillations cause mixing with ambient air or with supplemental oxygen. | Oscillations move very little gas. PACO$_2$ and PaCO$_2$ rises due to respiratory arrest. |
| Displaced nasal cannula | Measured PetCO$_2$ will be lower than PACO$_2$ due to mixing of the gas sample with ambient (non-alveolar) air | None |

TABLE 1-continued

| Source of etCO2 error | Effect on measured PetCO$_2$ | Effect on Alveolar CO$_2$ (PACO$_2$) and arterial CO$_2$ (PaCO$_2$) |
|---|---|---|
| High oxygen flow | Measured PetCO$_2$ will be lower than PACO$_2$ due to dilution of the alveolar gas sample with the supplemental oxygen flow. | None |
| Ventilation/perfusion mismatch, alveolar dead space, intrapulmonary shunt. | None, measured PetCO$_2$ matches alveolar PACO$_3$ | Alveolar PACO$_2$ and measured etCO$_2$ are lower than arterial PaCO$_2$ |
| Cardiac Arrest | Measured PetCO$_2$ should be equal to alveolar (PACO$_2$) if no other sources of error are present | PaCO$_2$ decreases as respiration clears CO$_2$ from the lung stores and no new CO2 is delivered from the blood. |

Note that all of the errors result in measured PetCO$_2$ being less than true alveolar CO$_2$ (PaCO$_2$). In the case of inadequate breath size, the measured PetCO$_2$ corresponds to a mix of alveolar gas and gas that remained in the anatomic dead space at the end of inspiration. This mixture will have a lower PCO$_2$ than that of a purely alveolar sample. In the case of a displaced nasal/oral cannula, the gas sampled by the capnometer is a blend of alveolar gas and ambient air/oxygen. Again, this mixture will have a lower PCO$_2$ than would be observed in a purely alveolar sample. In the case of excessive O$_2$ flow, the alveolar gas is diluted by the oxygen flow as it is being exhaled leading to a lower CO$_2$ concentration than a non-diluted alveolar sample. This oxygen dilution can occur using a split septum nasal cannula or when sampling using under an oxygen mask.

Cardiogenic oscillations occur when there is CO$_2$ in the mask or nares at the end of expiration and a protracted end-expiratory pause. During the end-expiratory pause, the beating of the heart causes very small movement of gas in the lungs. These small movements simulate small breaths (usually <20 ml) that do not cause any significant ventilation. However, since there is a large CO$_2$ concentration gradient between the end-tidal gas in nares and the nearby ambient air, only a very small volume is needed to bring ambient air to the sampling point in the nares and then re-fill the nares with alveolar gas. Because the capnometer only analyzes CO$_2$ concentration, and not volume, these small cardiogenic breaths can be confused by the capnometer with actual breaths. In any case, the end-tidal CO$_2$ measured due to cardiogenic oscillations will be no higher than the previous true etCO$_2$ measurement and will probably be lower due to mixing with the ambient air entrained into the nares by the cardiogenic breaths.

To account for these errors that are prone to CO$_2$ monitoring in non-intubated patients, the present inventors developed a filtering rule based on the following assumptions:

1) Arterial PaCO$_2$ is at least as high as the highest recorded airway PCO$_2$, and
2) There is a physical limit to how much the true alveolar PACO$_2$ can change from breath to breath.

With respect to the first assumption, for a non-intubated patient, PetCO$_2$ is used as an indicator of the trend of arterial CO$_2$ (PaCO$_2$). A high PetCO$_2$ is interpreted as indicating insufficient respiration that should be treated. Table 1 above lists a number of monitoring faults that cause end-tidal CO$_2$ to read low relative to PaCO$_2$. Table 1 also includes physiological conditions that cause alveolar and measured PetCO$_2$ to be lower than arterial PaCO$_2$. There is no condition that can cause the measured end-tidal CO$_2$ to be greater than the true arterial PaCO$_2$. Note: there on some rare conditions that can cause PetCO$_2$ to be slightly greater than measured PaCO$_2$, but then only by an insignificant amount of less than 3 mm Hg. So when the capnometer reads a maximum expired PCO$_2$ value observed during a breath, it is generally safe to assume that the arterial PaCO$_2$, is at least as high as that maximum measured value.

With respect to the second assumption, the amount of CO$_2$ in the lungs is increased by venous blood bringing CO$_2$ from the body tissues and is decreased by dilution when a volume of gas that does not contain CO$_2$ (or contains less CO$_2$) is inhaled. During stable ventilation, there is a balance between the CO$_2$ delivered to the lungs from the blood and the amount carried out of the lungs by ventilation. In this steady-state condition, the alveolar CO$_2$ concentration is stable. Because the volume of CO$_2$-containing gas stored in the lungs at the end of expiration (in the FRC) is generally about 4-6 times as large as a typical breath, and because a significant amount of CO$_2$ is stored in the tissues of the lung, it is impossible for the concentration of CO$_2$ in the lungs to change drastically in a single breath. Even if the blood flow to the lungs ceased, many breaths would be needed to completely clear the lungs of CO$_2$. Alternatively, if the maximum inspiratory tidal volume is inhaled, the concentration of exhaled CO$_2$ can change by no more than 50%. On the other hand, if ventilation stops completely, then alveolar CO$_2$ rises by 4-8 mm Hg to the venous CO$_2$ level over the course of 30-60 seconds and then increases much more slowly thereafter.

During normal ventilation, a 500 ml breath leads to 350 ml of alveolar ventilation. This breath causes a 3-10% decrease of the volume and concentration of CO$_2$ stored in the lungs. In the absence of ventilation, an equal increase in volume and concentration occurs during the period of a normal breath. It is unreasonable to expect that breath-to-breath changes in alveolar CO$_2$ (PACO$_2$) greater than this range should occur during normal (non-exercise) conditions. It is therefore reasonable to limit breath-to-breath changes in the reported end-tidal CO$_2$ to a similar range as defined by a fixed percentage of the previously reported value. The one exception to this is the case where the maximum CO$_2$ observed during the breath is greater than the PetCO$_2$ reported for the previous breath. In which case, the new maximum CO$_2$ should be reported as the PetCO$_2$.

Based on these assumptions, the present invention provides a filtering algorithm or rule to use when deciding which $PetCO_2$ to report or use for monitoring purposes. According to this rule, report the $PetCO_2$ as the greater of the either: (a) the maximum $CO_2$ observed during the breath, or (b) the $PetCO_2$ reported for the previous breath decreased by the maximum allowable breath-to-breath percent change. In an exemplary embodiment, the maximum percent change is between 3 and 10% (1-4 mm Hg)

When monitoring non-intubated patients, most of the observed breath-to-breath change in the maximum $PetCO_2$ during each breath is due to artifacts such as those listed in the table above. Following this rule reduces that chance that artificially low readings are either displayed directly, or are included into displayed average values. Either of these conditions would cause the capnometer to fail to detect a dangerously high $CO_2$ level caused by insufficient respiration thereby reducing the overall utility of capnometry and risking patient safety. Thus, the present invention improves the reliability of the output of the capnometer and, hence, increases the safety of the patient using the capnometer.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing an end-tidal gas value for a current breath comprising:
   measuring a plurality of gas concentration values;
   determining end-tidal gas values from the plurality of gas concentration values for a current breath and a previous breath which is previous to the current breath; and
   reporting the end-tidal gas value for the current breath as a greater of one of: (a) a maximum gas concentration values observed during the current breath, and (b) an end-tidal gas value reported for the previous breath decreased by a maximum allowable breath-to-breath percent change.

2. The method of claim 1, further comprising measuring a plurality of ventilation values, and wherein determining the end-tidal gas value is based, as least in part, on the ventilation values.

3. The method of claim 2, wherein the ventilation values measured are flow, volume, pressure, temperature, and humidity or any combination thereof.

4. The method of claim 2, wherein determining the end-tidal gas value includes applying a mathematical relationship to the ventilation values and the gas concentration values.

5. The method of claim 1, wherein the gas concentration values measured are carbon dioxide, oxygen, nitrous oxide, nitric oxide, and anesthetic agents or any combination thereof.

6. The method of claim 1, further comprising:
   measuring a plurality of ventilation values;
   determining the degree of ventilatory stability from the ventilation values; and
   providing an estimate of reliability of the end-tidal gas values using the degree of ventilatory stability.

7. A method of claim 1, further comprising:
   measuring a plurality of flow values;
   determining a plurality of volume values from the flow values;
   determining the degree of ventilatory stability from the flow values and volume values; and
   providing an estimate of reliability of the end-tidal gas values using the degree of ventilatory stability.

8. An apparatus for improving reliability of an end-tidal gas value for a current breath comprising:
   means for sensing a plurality of gas concentration values;
   means for determining end-tidal values from the gas concentration values for a current breath and a previous breath which is previous to the current breath; and
   means for reporting the end-tidal gas value for the current breath as a greater of one of: (a) a maximum gas concentration values observed during the current breath, and (b) an end-tidal gas value reported for the previous breath decreased by a maximum allowable breath-to-breath percent change.

9. The apparatus of claim 8, further comprising: means for sensing a plurality of ventilation values, and wherein the means for determining an end-tidal value determines the end-tidal gas value based, as least in part, on the ventilation values.

10. The apparatus of claim 9, wherein the means for determining the end-tidal gas value applies a mathematical relationship to the ventilation values and the gas concentration values.

11. The apparatus of claim 10, wherein the mathematical relationship is a power regression.

12. The apparatus of claim 8, wherein the gas concentration values measured are carbon dioxide, oxygen, nitrous oxide, nitric oxide, and anesthetic agents or any combination thereof, and wherein the ventilation values measured are flow, volume, pressure, temperature, and humidity or any combination thereof.

* * * * *